(12) United States Patent
Smith

(10) Patent No.: US 11,648,595 B2
(45) Date of Patent: May 16, 2023

(54) BIOLOGICAL CLEANUP KIT

(71) Applicant: Northfield Medical Manufacturing, LLC, Norfolk, VA (US)

(72) Inventor: Carter Champney Smith, Norfolk, VA (US)

(73) Assignee: Northfield Medical Manufacturing, LLC, Norfolk, VA (US)

( * ) Notice: Subject to any disclaimer, the term of this patent is extended or adjusted under 35 U.S.C. 154(b) by 0 days.

(21) Appl. No.: 17/533,570

(22) Filed: Nov. 23, 2021

(65) Prior Publication Data

US 2022/0088646 A1    Mar. 24, 2022

Related U.S. Application Data

(62) Division of application No. 16/243,836, filed on Jan. 9, 2019, now Pat. No. 11,207,714.

(Continued)

(51) Int. Cl.
*A47L 13/52* (2006.01)
*B08B 7/04* (2006.01)
(Continued)

(52) U.S. Cl.
CPC ............... *B08B 7/04* (2013.01); *A47L 13/02* (2013.01); *A47L 13/16* (2013.01); *A47L 13/52* (2013.01);
(Continued)

(58) Field of Classification Search
CPC ................................. A47L 13/51; A47L 13/52
(Continued)

(56) References Cited

U.S. PATENT DOCUMENTS 3,534,424 A    10/1970    Levinson
3,639,937 A    2/1972    Sweeney
(Continued)

FOREIGN PATENT DOCUMENTS

GB         2485443 A  *  5/2012
WO     2003078082 A1     9/2003
(Continued)

OTHER PUBLICATIONS

Medline Industries Inc., Medical Devices; QuickSuite disposable operating room clean up system launched, Science Letter, Dec. 21, 2004, 878, NewsRx, Atlanta, United States.
(Continued)

*Primary Examiner* — Randall E Chin
(74) *Attorney, Agent, or Firm* — Williams Mullen; F. Michael Sajovec

(57) ABSTRACT

The present disclosure relates to a kit for cleaning biological fluids from a surface. The kit comprises at least one protective article of clothing, absorbent powder, a trash bag, surface sanitizer, an absorbent towel, a scraper, a handle, and a dustpan. The dustpan is configured to be securely coupled to the handle. The dustpan has a lid and a base and can alternate between an open position and a self-sealing closed position. In the closed position the base and lid define an interior volume having a height along a y-axis, a width along an x-axis, and a depth along a z-axis. An adhesive strip is coupled to a lip of the dustpan and is configured to interact with a surface and temporarily engage the dustpan with the surface. The absorbent powder is a mixture of a super absorbent polymer and perlite.

9 Claims, 17 Drawing Sheets

Related U.S. Application Data

(60) Provisional application No. 62/718,457, filed on Aug. 14, 2018, provisional application No. 62/615,222, filed on Jan. 9, 2018.

(51) Int. Cl.
| | | |
|---|---|---|
| *B08B 3/10* | (2006.01) | |
| *B08B 7/00* | (2006.01) | |
| *B08B 1/00* | (2006.01) | |
| *B08B 13/00* | (2006.01) | |
| *A47L 13/02* | (2006.01) | |
| *A47L 13/16* | (2006.01) | |
| *B09B 3/10* | (2022.01) | |
| *A61L 2/18* | (2006.01) | |

(52) U.S. Cl.
CPC ............ *B08B 1/005* (2013.01); *B08B 3/10* (2013.01); *B08B 7/0014* (2013.01); *B08B 13/00* (2013.01); *B09B 3/10* (2022.01); *A61L 2/18* (2013.01); *B08B 1/006* (2013.01)

(58) Field of Classification Search
USPC .............................................. 15/257.1, 257.9
See application file for complete search history.

(56) References Cited

U.S. PATENT DOCUMENTS

| | | |
|---|---|---|
| 4,186,955 A | 2/1980 | Campbell |
| 4,230,354 A | 10/1980 | Claras |
| 4,809,390 A * | 3/1989 | Jackson ............... A47L 13/52 294/1.3 |
| 4,917,238 A | 4/1990 | Schumacher |
| 6,249,930 B1 | 6/2001 | Noggle |
| 7,150,118 B1 | 12/2006 | Benton et al. |
| 7,731,031 B1 | 6/2010 | Weinberger |
| 9,004,555 B1 | 4/2015 | Chirico |
| 2007/0151065 A1 | 7/2007 | Monahan et al. |
| 2010/0065448 A1 | 3/2010 | Vargas |
| 2013/0192631 A1 | 8/2013 | Scoralle |
| 2019/0150698 A1 | 5/2019 | Gregory et al. |
| 2019/0200834 A1 | 7/2019 | Olschan et al. |

FOREIGN PATENT DOCUMENTS

| | | |
|---|---|---|
| WO | 2007053690 A2 | 5/2007 |
| WO | 2018183317 A1 | 10/2018 |

OTHER PUBLICATIONS

3M UK PLC, 3M cleans up with new disposable spill kit, Food Trade Press Ltd., Magazine/Journal, Nov. 2006-Dec. 2006 [retrieved on Nov. 14, 2018], 667(1), vol. 76, ProQuest Dialog.

* cited by examiner

BIOLOGICAL CLEANUP KIT

CROSS REFERENCE TO RELATED APPLICATIONS

This divisional application claims priority to U.S. application Ser. No. 16/243,836, filed Jan. 9, 2019, now allowed as U.S. Pat. No. 11,207,714, which claims the benefit of U.S. Provisional Application No. 62/718,457, filed Aug. 14, 2018, and U.S. Provisional Application No. 62/615,222, filed Jan. 9, 2018, the contents of which are incorporated by reference in their entireties.

STATEMENT REGARDING GOVERNMENT SUPPORT

None.

FIELD

This disclosure relates to kits that include tools and supplies for the cleanup of certain biological materials or spills; more particularly, such kits may be directed to assist personnel in responding to and cleanup from an event, such as emesis, while protecting the responding personnel and those within the facility.

BACKGROUND

In the event of a spill of bodily fluids, such as customer vomiting in a retail establishment, the use of a spill or cleanup kit may help contain the fluid and protect both customers and employees within the establishment. Some providers have assembled or collected certain tools and supplies for response, such as conventional paper towels, trash bags, gloves, and in some cases, absorbent powder or granules, a broom, and a conventional dustpan. Commonly, chlorine or sodium hypochlorite has been used for disinfection.

In most kits, supplies such as paper towels or absorbent powder may be disposable, but the clean-up tools are intended for re-use and are not disposable. These tools are often plastic, metal, or wood. A broom or dust pan, or scoop should be cleaned after use. In some cases, perhaps a disposable plastic scoop may be provided, but the other tools are not. Such elements are typically either re-usable (which requires cleaning or risks cross-contamination) or, if an item such as a disposable scoop is provided, the material cost drives up the price of the overall kit.

A notable problem that could arise with a dustpan or hard scoop is that it can permit or allow spilled material to spread (i.e., pass underneath or around the dustpan). The dustpan forms an imperfect seal with the floor or underlying surface. In addition, in some cases the disinfecting material may spread the material, or counteract the operation of absorbent powder by introduction of liquid. Common cleaners may not be effective, or if they are effective, may have harmful side effects. In some cases, the use of common multipurpose disinfectants may be hampered by a long pathogen kill time.

Other shortcomings of conventional approaches are that kits may be inadequate or not scalable for large spill incidents. Many kits may require the user to work within inches of potentially infectious spill matter.

It would be desirable to provide a low cost kit of supplies and equipment that avoids or reduces the effects of such problems. In addition, it would be desirable to have a safe kit that protects users and others, while being environmentally friendly or biodegradable.

BRIEF SUMMARY OF THE INVENTION

Disclosed are embodiments and/or features of a portable cleanup kit having inexpensive and disposable components for cleaning biological spills. The kit includes a number of innovations, such as disposable, portable waste containers, improved collection devices or dust pans, foldable components, and an overall inexpensive, disposable assemblage, that is almost entirely biodegradable and landfill-friendly. Included are methods or processes for using or employing such components.

In one embodiment, a kit for cleaning biological fluids from a surface is provided. The kit comprises at least one protective article of clothing, absorbent powder, a trash bag, surface sanitizer, an absorbent towel configured to be used to wipe up the surface after the absorbent powder had absorbed the bodily fluids and had been disposed of, a scraper, a handle, and a dustpan. The dustpan is configured to be securely coupled to the handle. The dustpan has a lid and a base, and is further configured to be alternated between an open position and a self-sealing closed position. In the closed position, the base and lid define an interior volume having a height along a y-axis, a width along an x-axis, and a thickness along a z-axis. An adhesive strip is coupled to a lip of the dustpan, the adhesive strip configured to interact with a surface and temporarily engage the dustpan with the surface. The absorbent powder is a mixture of a super absorbent polymer and perlite.

In another embodiment, a dustpan for use in cleaning and retaining spills of biological fluids is provided. The dustpan comprises a back panel, a front panel, a top panel, a bottom panel, and two side panels that, when in a closed position, define an interior volume having a height along a y-axis, a width along an x-axis, and a thickness along a z-axis. The dustpan has a base portion and a lid portion, a threaded coupling configured to secure a handle to the dustpan, and an adhesive strip coupled to the base portion proximate a lip of the bottom panel and covered by a liner. The adhesive strip has a super-absorbent polymer proximate edges of the tape wherein the super-absorbent polymer is configured to react with moisture and form a barrier to seal the edges of the tape to a surface. The top panel is configured to extend along an x-y plane and has an exterior surface, a front edge, a rear edge, and a midpoint between the front edge and the rear edge. A hinge point secures the lid portion to the base portion. The front panel is configured to extend along an x-y plane, and has a top edge, a bottom edge, and two side edges. The front panel is connected to two side panels of the lid at each of the side edges. The dustpan is configured to alternate between a self-sealing closed position and an open position. In the open position, the lid portion rotates about the hinge point.

In yet another embodiment, a dustpan is provided for cleaning and retaining spills and biological fluids that alternates between a closed position and an open position. The dustpan comprises a base having a top panel, a rear panel, a bottom panel, and two side panels, a lid having a front panel and two side panels, the lid and the base having a height along a y-axis, a width along an x-axis, and a thickness along a z-axis, a hinge point connecting the base to the lid, a secure coupling configured to attach a handle to the dustpan, the secure coupling coupled to the lid, and an adhesive strip coupled to the bottom panel proximate a lip of the bottom panel and covered by a liner. The adhesive strip has been treated with a super-absorbent polymer proximate edges of the adhesive strip wherein the super-absorbent polymer is configured to react with moisture and form a barrier to seal the edges of the adhesive strip to a surface. The hinge point connects the base top panel to the lid top panel and allows the lid and base to rotate about the x-axis as the dustpan alternates between an open position and a closed position. The handle is coupled to the lid such that when the dustpan is lifted using the handle from the open position on the ground, and the dustpan is configured to self-seal and alternate to the closed position.

DESCRIPTION

Figure 1:
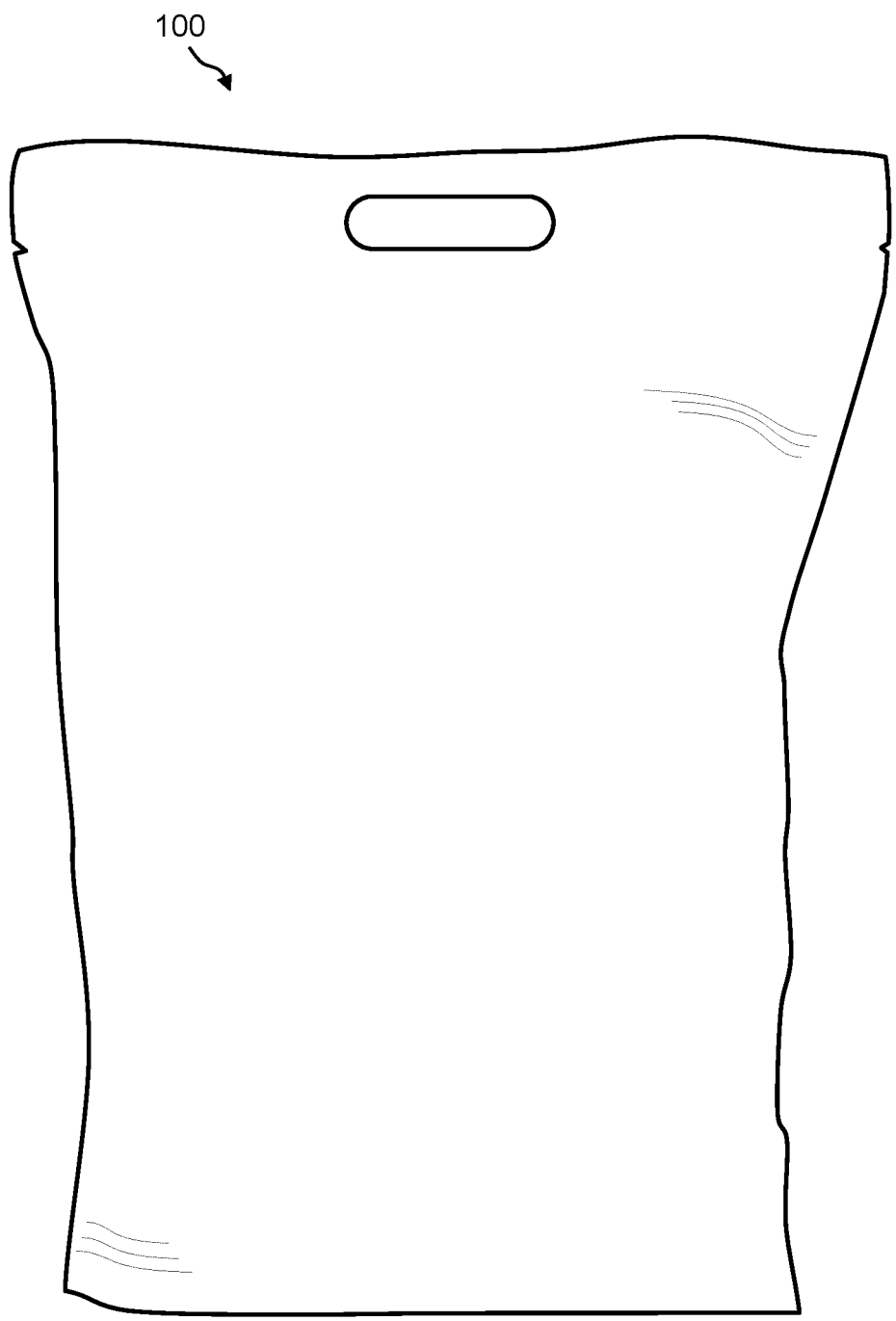
FIG. 1 shows a kit according to the present approach in a packaged embodiment.

The present invention now will be described more fully with reference to the accompanying drawings, in which embodiments of the invention is shown. However, this invention should not be construed as limited to the embodiments set forth herein. Rather, these embodiments are provided so that this disclosure will be thorough and complete, and will fully convey the scope of the invention to those skilled in the art.

As used herein, the term "comprising" or "comprises" is open-ended, and includes one or more stated features, integers, elements, steps, components or functions but does not preclude the presence or addition of one or more other features, integers, elements, steps, components, functions or groups thereof. As used herein, the term "and/or" includes any and all combinations of one or more of the associated listed items. The term "about" means the stated value plus or minus a reasonable or conventional margin of error of measurement, or plus or minus 10% if no method of measurement is indicated.

As used herein, the common abbreviation "e.g.," which derives from the Latin phrase "exempli gratia," may be used to introduce or specify a general example or examples of a previously mentioned item, and is not intended to be limiting of such item. If used herein, the common abbreviation "i.e.," which derives from the Latin phrase "id est," may be used to specify a particular item from a more general recitation.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Well-known functions or constructions may not be described in detail for brevity and/or clarity. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, spatially relative terms, such as "under," "below," "lower," "over," "upper," "downward," "upward," "inward," "outward" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

It will be understood that when an element is referred to as being "attached," "coupled" or "connected" to another element, it can be directly attached, coupled or connected to the other element or intervening elements may also be present. In contrast, when an element is referred to as being "directly attached," directly coupled" or "directly connected" to another element, there are no intervening elements present. Words such as passageway, fluid path, or flow component, etc., are intended to communicate structure supporting fluid communication and may comprise a tube, pipe, hose, boring, channel, etc.

The U.S. Food Code includes recommendations of the U.S. Publish Health Service and the Food and Drug Administration. Changes made in 2013 amended the Food Establishment Inspection Report to include procedures for responding to vomiting and diarrheal events. This code also specifies single-use cleaning supplies for such body fluid events to reduce food borne illnesses.

Examples or embodiments of the present spill kit introduce several novel advances over conventional approaches. Conventional spill kits typically required the use of a larger disinfectant bottle designed to be used for many spill cleanups. This creates a cross-contamination risk (e.g., Norovirus can live on surfaces for up to two weeks). In addition, many conventional components are plastic, off-the-shelf items intended for re-use, such as plastic dust pans. The present approach is intended to be single use, disposable, and about 80% biodegradable. The present kit 100 may contain a flat trash bin 10, a waste bag 20, absorbent powder 30, single-use bottles of disinfectant or surface sanitizer 40, protective equipment or clothing articles 90, a handle or pole extension 65, as well as single use components that eliminate the risk of cross-contamination. Components may include paper-based tools such as a floor scraper 70, boxes that are configured to fold into a trash bin 10, mop pads or other absorbent towels 60, non-leaching absorbents 80, and disinfectants 10, such as EPA Category 4 disinfectants (the safest environmental designation available). A paper based dustpan 500 or scoop includes an adhesive strip 510 that forms an adhesive seal that overcomes the challenge of debris sliding under the dustpan 500 and remaining on the floor. This adhesive strip 510 also enables the dustpan 500 to be used in a hands-free basis, so the person cleaning the spill may use both hands to scrape and mop the site. Another component is a perlite and/or superabsorbent polymer absorbents that binds with liquid waste in a non-leaching bond. This is contrary to paper towels or other paper-based absorbents, which leach liquids under pressure. This non-leaching absorbent reduces the risk of cross-contamination, protects employees better during cleanup, and is accepted by landfills in all U.S. states. In addition, the non-leaching molecular bond of the absorbents reduces or eliminates a risk of airborne particulates being kicked up and dispersed during cleanup. Norovirus has been known to travel up to 25 feet from a spill site. In addition, examples of kits may include clean up tools (scraper, mops, dustpans) with handles suited for the application, including handles of varying lengths. Conventional tools require the person cleaning to closely approach a spill, as with the use of paper towels, hand scrapers, etc. where hand/glove contact with the waste is likely. In larger-format examples of kits, handle segments 65 may be interchangeable, allowing one pole 65 to function as a long handle on multiple tools throughout cleanup, reducing kit cost and landfill waste.

Cleanup Kit Example 1

The present approach is a spill cleanup kit improved in novel ways over conventional approaches. FIG. 1 shows a first example of the present cleanup kit 100, shown in an original package. Other forms of packaging and presentations may be used. In some embodiments, there may be a convenient hand grip for transportation to a site of use. Note also the compact nature of the packaged kit 100, which is enabled by the design and material of the included components. A clear package may enable a quick review of the contents, such that a user may supplement the contents if desired.

Figure 2:
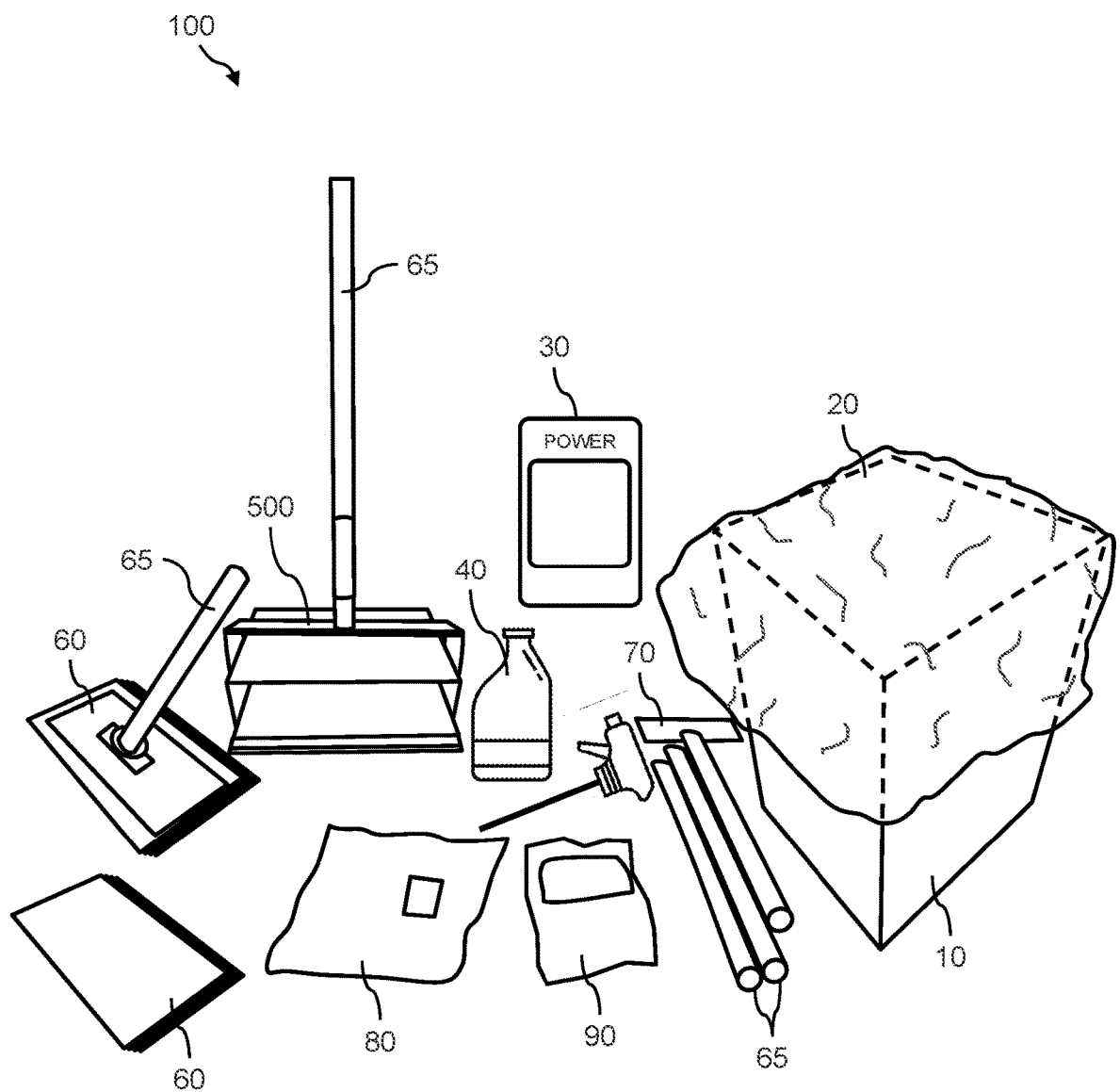
FIG. 2 shows the kit according to claim 1 in an unpackaged embodiment fully displaying the contents of the kit.

FIG. 2 is a view of the cleanup kit 100 items displayed outside of their original package, with certain kit elements or contents assembled for use. A foldable waste or trash bin 10 is shown in a cardboard embodiment, which enables it to pack flat until use; while other materials, such as light, plastic boards may be used, cardboard has been found to be lightweight, easily assembled, inexpensive, disposable and easily biodegradable. The originally flat trash bin 10 may be unfolded or assembled into its useable configuration, with a trash or waste bag 20 inserted. Cleanup kit 100 may include a desired number of waste bags 20, depending on the contemplated use, and three waste bags 20 may be provided.

This embodiment of cleanup kit 100 may have an absorbent powder 30, such as an amorphous alumina silicate perlite and/or a superabsorbent polymer, such as a Sodium polyacrylate superabsorbent under the Absorb! brand name. The cleanup kit 100 may further include an ethyl alcohol based foodservice grade surface sanitizer 40, such as those available from GOJO Industries, Inc. under the Purrell® brand name. Mop 60, with pole extensions 65 may also be seen, along with floor scraper 70, and a pouch with personal protective equipment 90. Pole extensions 65 and tools may be configured in a standard size and mating design, such that the extensions 65 may be used interchangeably with any of the tools, if desired.

Optionally, cleanup kit may also include swabs or sanitary cloths or "singles" having alcohol for user cleaning. A user, for example, may thoroughly wash hands for a desired period (e.g., 15-20 seconds) and then use cloths to disinfect hands. When spill site is completely dry, users may discard warning signs and reopen the affected area for personnel access.

Figure 3:
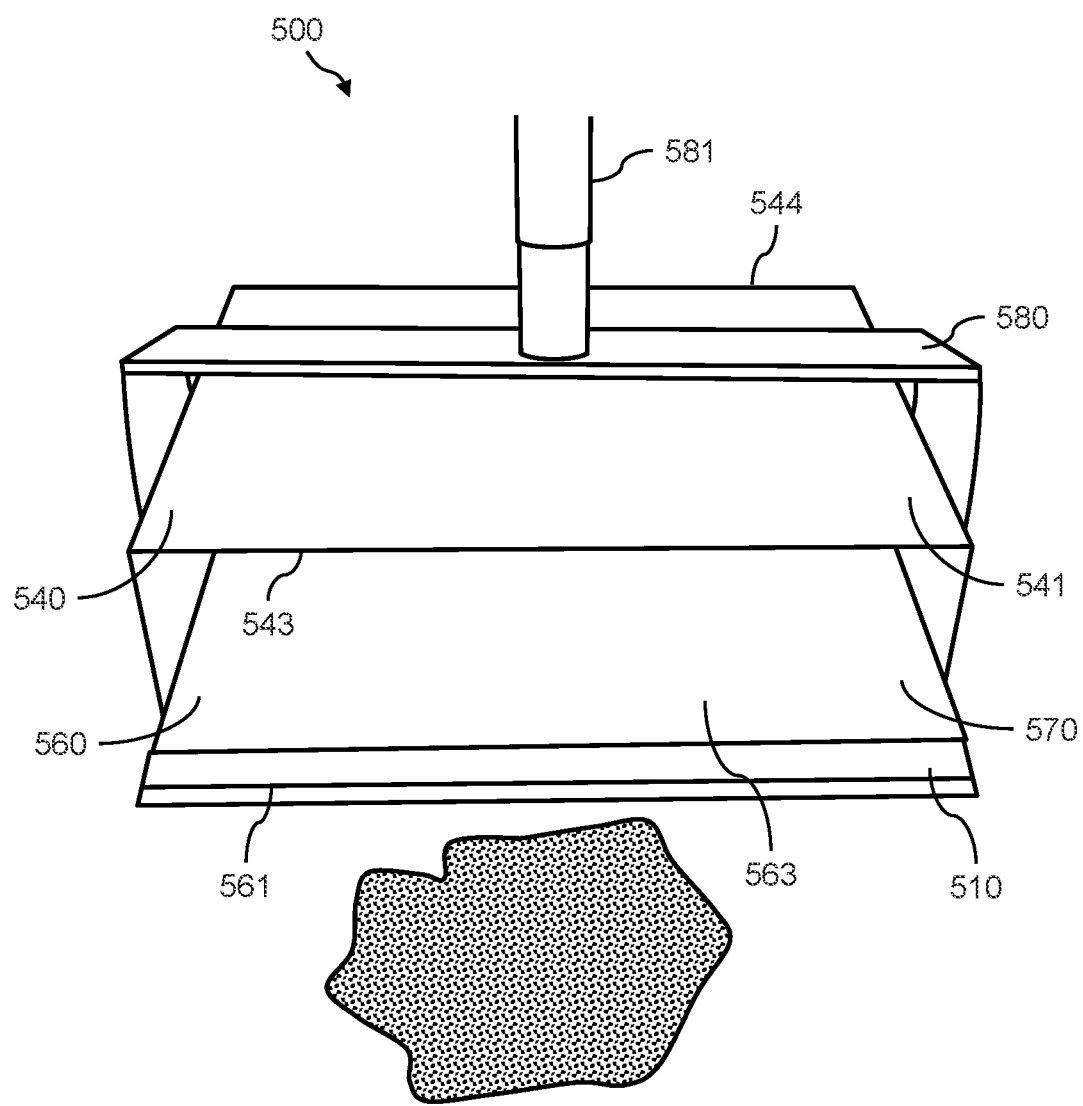
FIG. 3 is a front view of a dustpan according to one embodiment in an open configuration.
Figure 4:
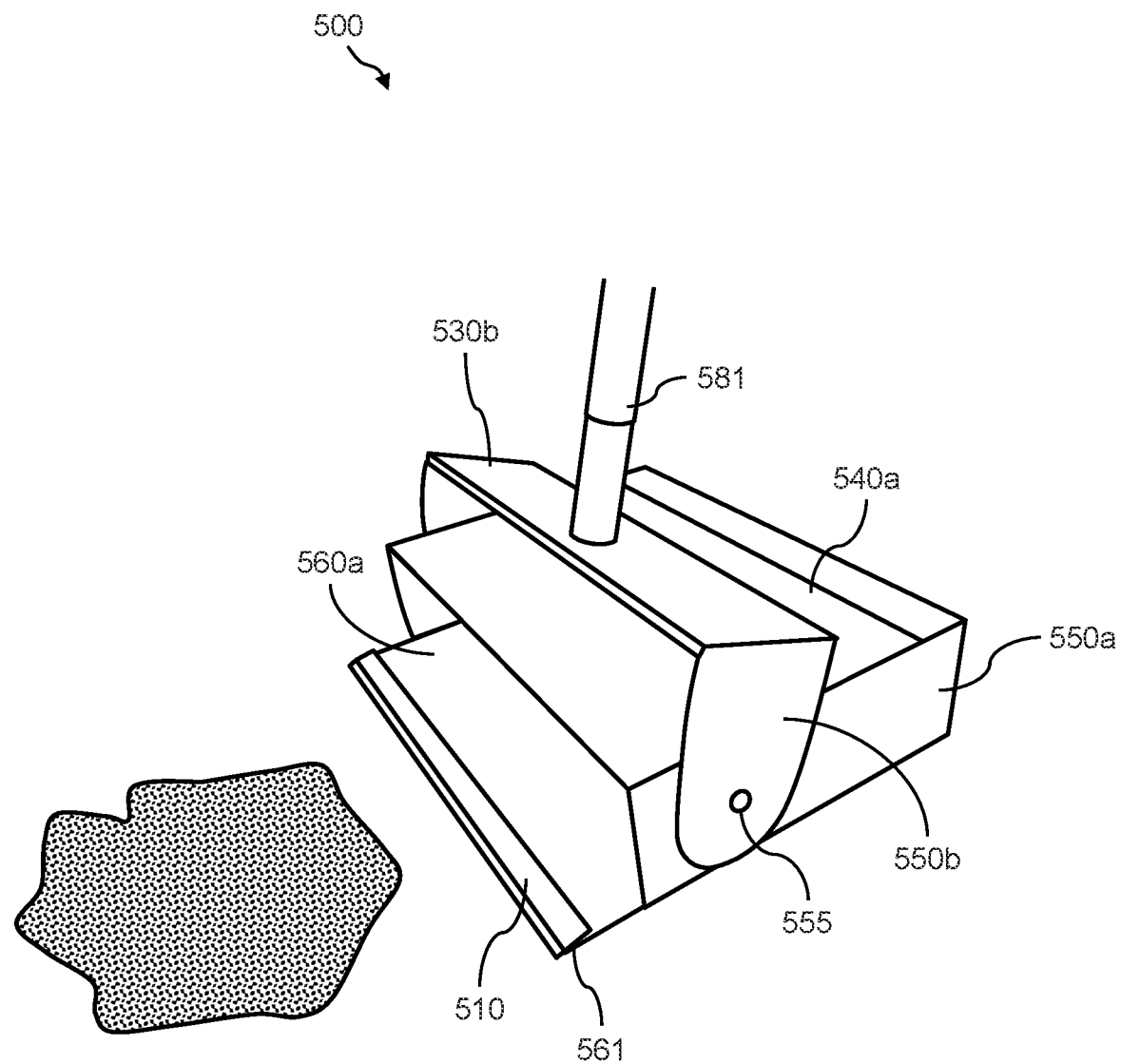
FIG. 4 is a perspective view of the dustpan in an open configuration.

Dustpan 500 may be assembled for use. Additional features or design elements for dustpan 500 will be described below; however, note that this embodiment may also be foldable cardboard, enabling the compact packaging of cleanup kit 100. As is shown in FIGS. 3 and 4, the dustpan 500 may be adhered to a surface proximate a spill and configured in an open position.

In some embodiments, a pouch labeled "OPEN FIRST" containing personal protective equipment 90 for the user may be provided. Cleanup kit 100 may include easy to understand instructions, such that even a user without training or experience may understand a safe and effective approach to cleanup of a spill. The kit 100 may instruct the user to don personal protective equipment 90 first, which may include equipment tailored for the contemplated use (e.g., an apron, face mask, gown, booties/shoe covers, respirator mask, etc.). Gloves may be donned last. Personal protective equipment 90 may, as applicable, be fabricated from vinyl, laminated papers, latex, nitrile, etc., as desired for the application. It is contemplated that inexpensive, effective, and disposable material will decrease the expense of kit 100. After donning personal protective equipment, kit 100 may contain instructions for the user to deploy optionally included foldable, single-use caution signs 80, for example, approximately ten feet from the site of the spill.

The flat trash bin 10 may be assembled into an upright position near the edge of a spill. Note that trash bin 10 and waste bags 20 may be configured such that waste bags 20 fit snugly over an opening of the assembled bin 10. It has been discovered that cardboard provides a material that can be deformed during the placement or insertion of a bag 20, with the ability to return to original dimensions for secure and safe retention of the bag 20 in place.

The bag containing absorbent powder 30 may be opened and its contents sprinkled to cover the spill with absorbent powder, as needed. In some embodiments, the bottle of disinfectant sanitizer 40 may be opened and applied to the spill site. The user may then wait a desired period, such as 30-seconds, for the sanitizer 40 and absorbent powder 30 to mingle with the spilled materials.

In some embodiments, dustpan 500 is configured to be disposable, self-closing, and configured with advantageous, integrated sealing tape 510. Dustpan 500 may be connected or attached to pole extensions 65 for use. Alternatively, if needed, the handle 65 may be telescoping—although the current embodiment is contemplated to be less expensive. Sealing tape 510 in its integrated form can be used to seal the lip of dustpan 500 to a surface to prevent leakage. Alternately, sealing tape 510 may be coupled to a bottom surface of the dustpan 500 proximate the lip. Sealing tape 510 may include a protective tape cover 515, liner, or backing, which may be removed for use. With tape cover 515 removed, dustpan 500 may be positioned at a suitable point proximate to the spill. The user may, for example, use a foot or other tool to attach the dustpan 500 to the floor.

Embodiments of cleanup kit 100 may also include a floor scraper 70, which also may be configured to attach to segments of pole extensions 65. Floor scraper 70 may be used to slide or drive more solid spill matter into dustpan 500. After all solid matter has been pushed into dustpan 500, the user may remove scraper 70 from pole extension 65 and dispose scraper 70 in waste bin 10.

With solid matter from the spill collected within dustpan 500, the user may then lift the self-closing dustpan 500 from the floor; sealing tape 510 may be configured for gentle removal from most surfaces, while also providing an effective seal during use. The dustpan 500 may also be disposed of into waste bin 10 (optionally, with removal of pole extension 65).

Many alterations and modifications may be made by those having ordinary skill in the art. If needed, the user may remove and replace the waste bag 20 from waste bin 10. A waste bag 20 that is full or no longer needed may be tied shut and set it aside. Any new bag 20 needed may be inserted within upright cardboard trash bin 10.

With all solid matter removed from a spill, a user may apply sanitizer 40 to thoroughly saturate entire spill site and wait a desired period, such as 30 seconds.

The user may then locate mop 60 and, if applicable, attach its segments of pole extensions 65. Mop 60 may be used to wipe the surface of spill site. If desired, the user may use all remaining sanitizer 40, optionally with sanitizer spray, to disinfectant and saturate the spill site and allow it to air dry. An empty container for sanitizer 40 may similarly be disposed within trash bag 20 in trash bin 10.

At this point, a user may also remove all protective personal equipment 90 and dispose the protective personal equipment 90. The user may lift the second waste bag 20 and tie it shut. If desired, a user may double-bag all waste, as with a three-waste bag 20 embodiment. If desired, the user may place first two bags 20 and any remaining items from cleanup kit 100 in third bag 20, then tie the bag shut and dispose of it in an appropriate place.

As is shown in FIGS. 3-13, the dustpan 500 may comprise a back panel 520, a front panel 530, a top panel 540, and two side panels 550. The dustpan may further comprise a bottom panel 560. The dustpan 500 may also have a base 570 and a lid 580. When in a closed position, the back panel 520, front panel 530, top panel 540, and side panels 550 form a substantially rectangular prism and define an interior volume that has a height along a y-axis, a width along an x-axis, and a thickness along a z-axis.

In some embodiments, the base 570 is a unitary construction. For example, the base 570 may be configured from a single piece of cardboard or other material that has been manipulated to form the various panels of the base 570. In contrast, the base 570 may be constructed from multiple pieces of cardboard that are coupled together. The lid 580 may similarly be a unitary construction.

The back panel 520 and front panel 530 may be configured to extend in an x-y plane. The side panels 550 may be configured to extend in a y-z plane. The top panel 540 and bottom panel 560 may be configured to extend in a x-z plane. The front panel 530 may have a top edge 531, a bottom edge 532, and two side edges 533.

The top panel 540 may further have an exterior surface 541, an interior surface (not shown), a front edge 543, a rear edge 544, a midpoint 545 between the front edge 543 and the rear edge 544. The dustpan 500 may also have a hinge axis. The hinge axis may run along an x-axis, and may be located laterally between the midpoint 545 and the front edge 543, and vertically between the top panel 540 and the bottom panel 560. The base 570 may be rotatably coupled to the lid 580 at a hinge point 555.

The base 570 may have a top panel 540a, a back panel 520a, two side panels 550a, and a bottom panel 560a. The base 570 may be a substantially rectangular shape. The top panel 540a and bottom panel 560a may be configured to extend in a x-z plane. The side panels 550a may be configured to extend in a y-z plane. The back panel 520a may be configured to extend in a x-y plane.

Figure 5:
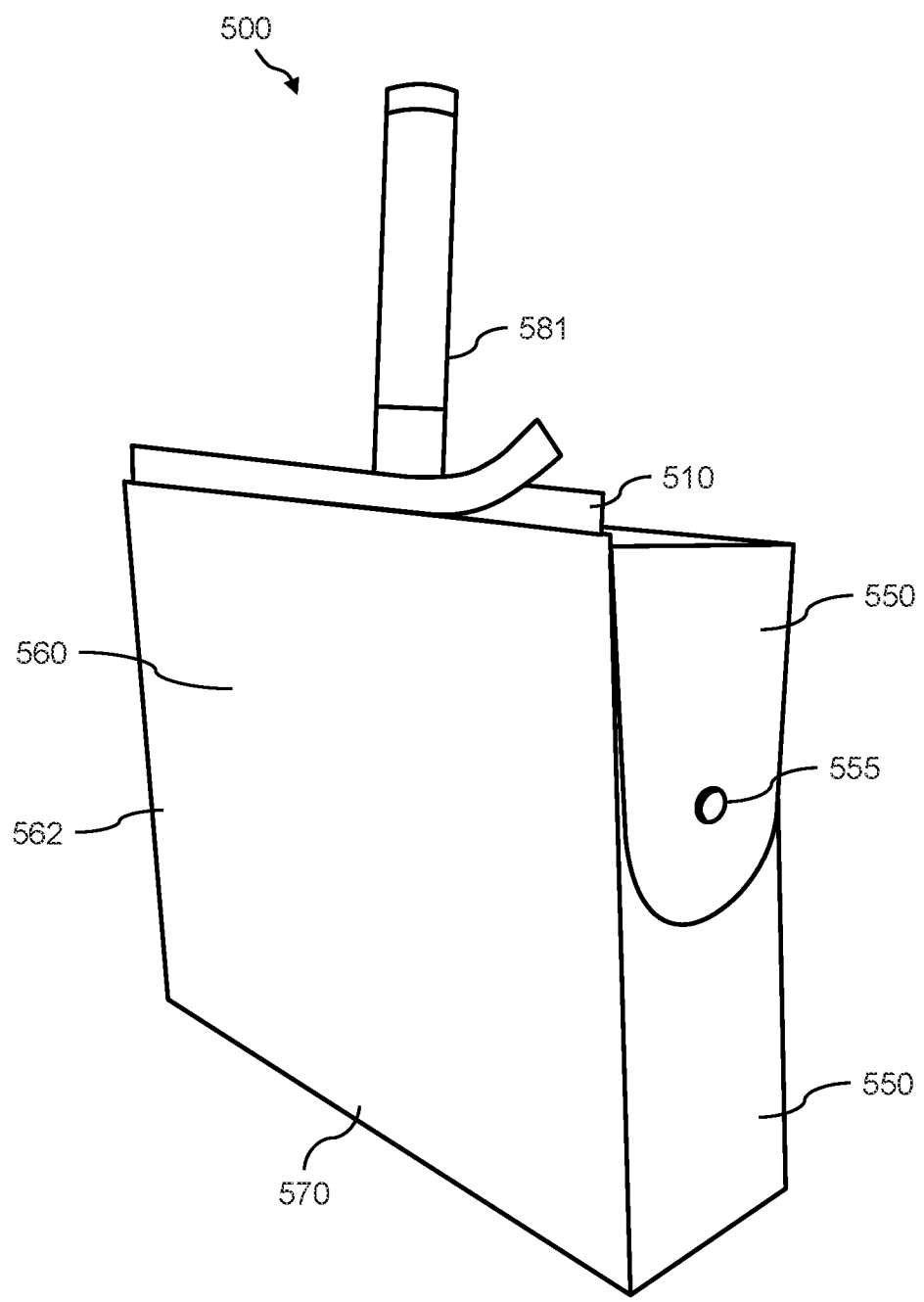
FIG. 5 is a bottom view of the dustpan with an adhesive strip.

As is shown in FIG. 5, the bottom panel 560a of the base may have a lip 561, a floor engaging surface 562, and an interior surface 563. Alternately, the bottom panel 560 of the dustpan 500 may have a lip 561. The adhesive strip 510 may be located proximate the lip 561. In some embodiments, the adhesive strip 510 is coupled to the floor engaging surface 562. Alternately, the adhesive strip 510 may be coupled to the interior surface 563 proximate and overhanging the lip 561. This embodiment may provide a tight seal that could avoid any biological waste material from being pushed beneath the dustpan 500.

The adhesive strip 510 may be a double sided adhesive strip. Alternately, the adhesive strip may be single-sided, but with a peel-off split-back design, which may enable a first end of the adhesive strip to be coupled to the dustpan 500 before the consumer receives the kit 100. In other embodiments, a first side of the adhesive strip has already been adhered to the dustpan 500 before the consumer receives the kit 100. In alternate embodiments, the adhesive strip 510 may be unattached to the dustpan 500. In such an embodiment, a user would adhere the first side of the adhesive strip 510 to the dustpan 500, and would then adhere a second side of the adhesive strip 510 to a surface near a biological spill. In some embodiments, the adhesive strip 510 is coupled to the dustpan 500 and extends along an x-axis.

The adhesive strip 510 may have two edges 513 that define a length of the adhesive strip 510 and extend along an x-axis. In some embodiments, the edges of the adhesive strip 510 have been treated with a super-absorbent polymer that reacts with water and gels to form a barrier that seals the edges of the adhesive strip 510, preventing moisture from seeping under the adhesive strip 510. In some embodiments, the adhesive strip 510 may be contain super-absorbent polymers, such as adhesive strips available from Shurtech Technologies, LLC under the FROGTAPE® brand name. Alternately, the single-sided adhesive strip 510 with a peel-off split-back design was specially designed for the present embodiment.

The lid 580 may have a front panel 530b and two side panels 550b. The front panel 530b may have a top edge 531b, a bottom edge 532b, and two side edges 533b. The side edges 533b may define part of a corner where the side panels 550b and the front panel 530b connect. In some embodiments, the lid 580 also has a top panel 540b. The top panel 540b may be advantageous in allowing the lid 580 to more freely pivot about the hinge point 555. In these embodiments, the top panel 540b of the base may come together with the top panel 540a of the lid in a closed configuration. The lid 580 may also have a bottom panel 560b. The lid 580 may be substantially rectangular in shape. The side panels 550b may be configured to extend in a y-z plane. The front panel 530b may be configured to extend in a x-y plane. In some embodiments, the top edge 531b and the bottom edge 532b are free and unattached to the dustpan 500.

In some embodiments the front panel 530b may also be configured to be curved. In those embodiments, the curved front panel 530b may be easier to manipulate between an open position and a closed position. In some embodiments, the side panels 550a of the base 580 may also be slightly curved, and the top panel 540a of the base may have a length along the y-axis that is shorter than a length of the bottom panel 560a of the base 580. These embodiments may allow for a tighter seal when the dustpan 500 is in a closed, self-sealing position.

The side panels 550b may have a shorter length along a z-axis than the side panels 550a of the base 570. In some embodiments, the side panels 550b of the lid 580 are less than one half a length of the side panels 550a of the base 570. The side panels 550b of the lid 580 may be between one-fourth and one-third a length of the side panels 550a of the base 570. The side panels 550b may be substantially rectangular, and a rear edge 551 of the side panels 550b may be substantially parallel to a bottom edge 552 and a top edge 553. In other embodiments, the rear edge 551 may be curved.

Figure 6:
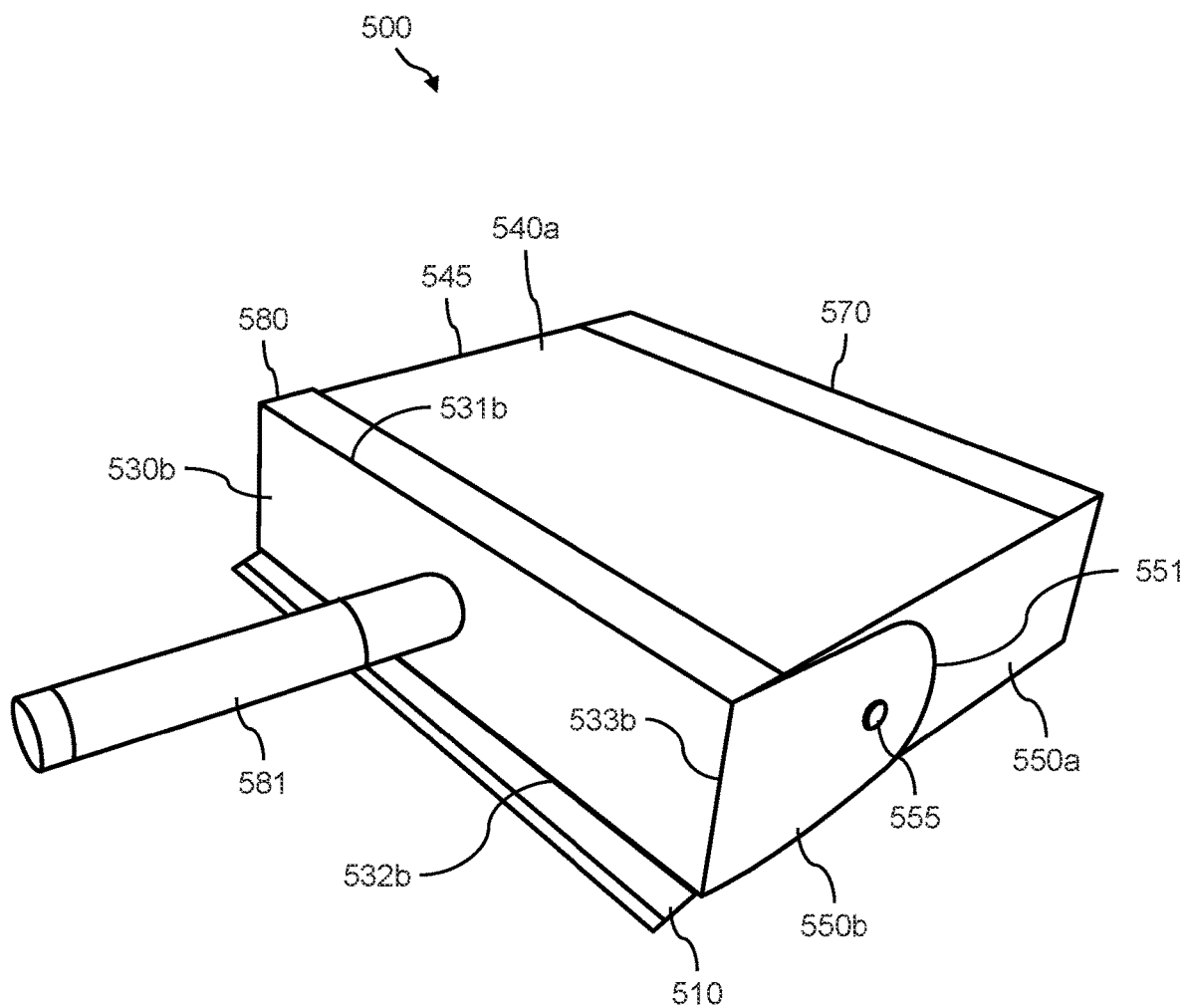
FIG. 6 is a perspective view of the dustpan in a closed configuration.
Figure 7:
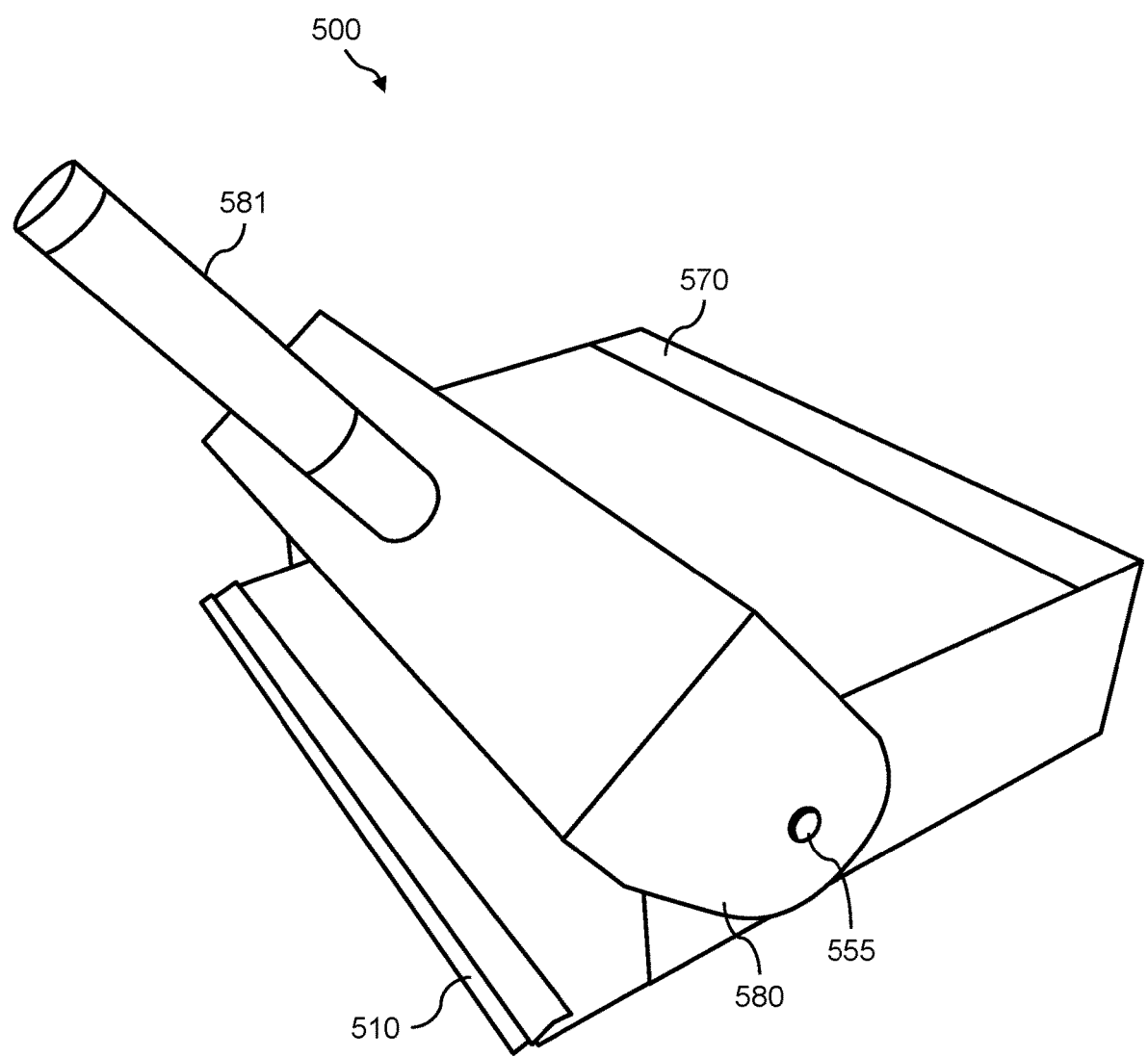
FIG. 7 is a perspective view of the dustpan as it is alternating between a closed configuration and an open configuration.
Figure 8:
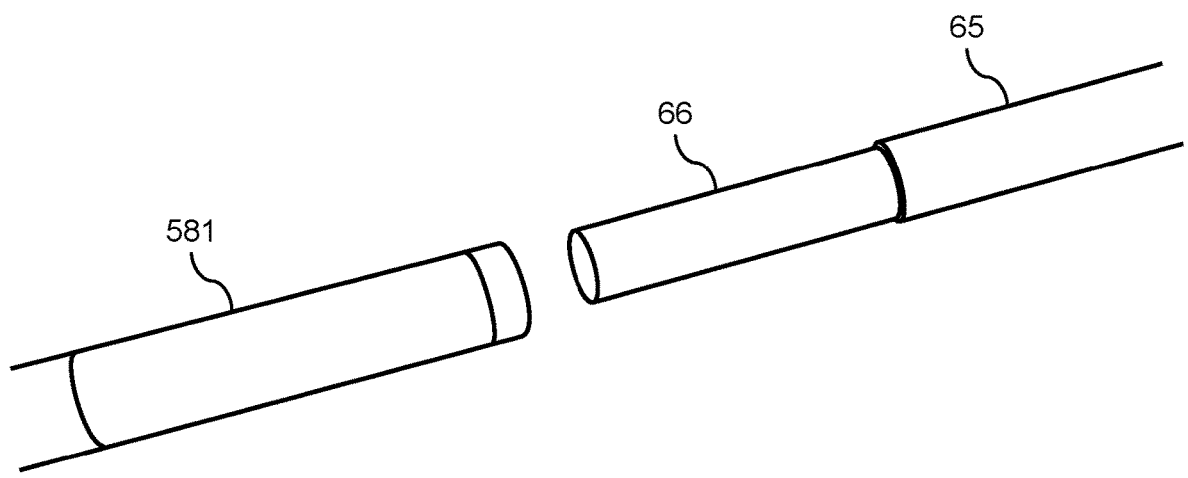
FIG. 8 is an exploded view of the dustpan and handle coupling.
Figure 9:
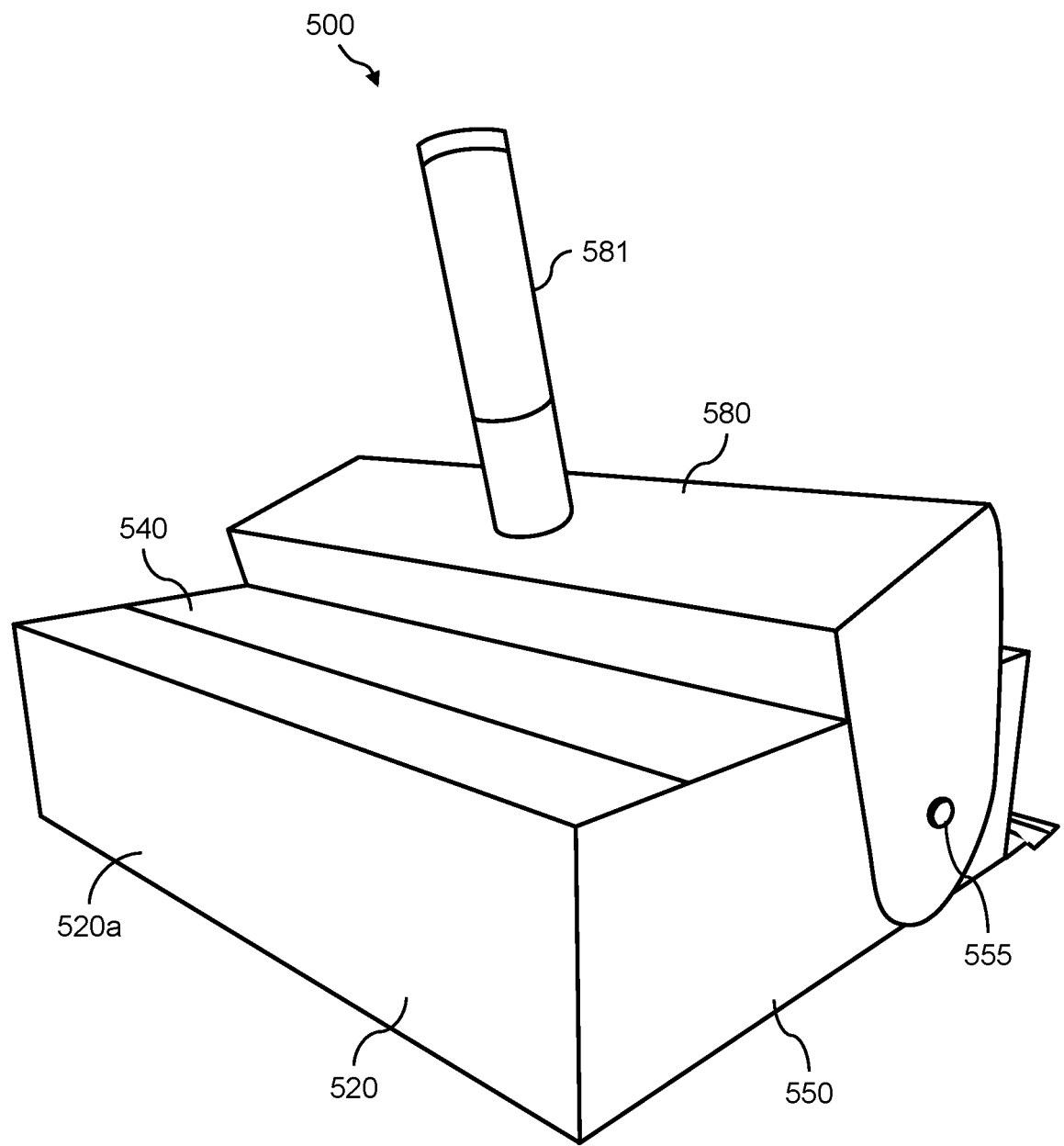
FIG. 9 is a rear perspective view of the dustpan.
Figure 10:
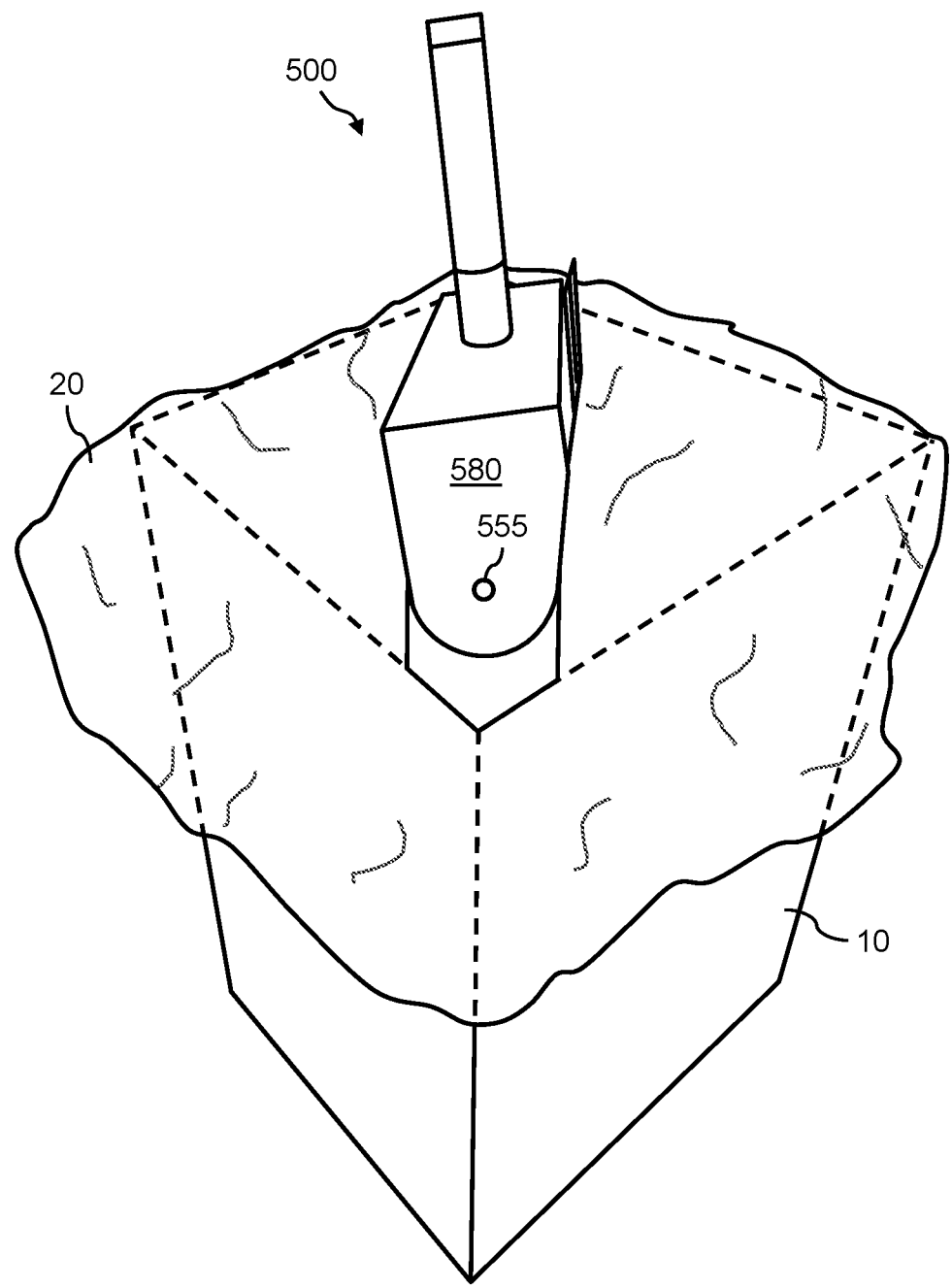
FIG. 10 is a perspective view of the dustpan being emptied into the trash.
Figure 12A:
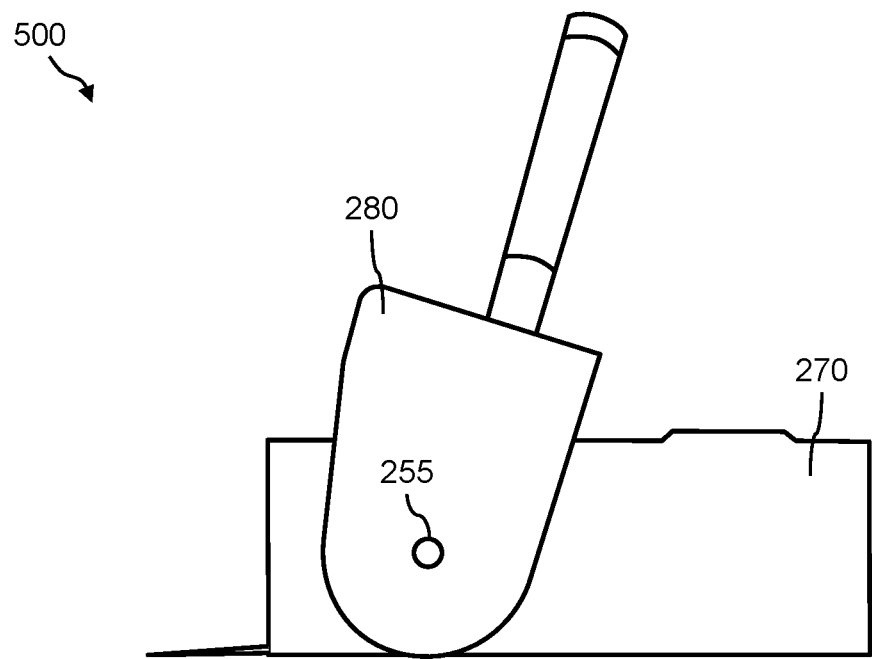
FIG. 12a is a side view of the dustpan in an open configuration.
Figure 12B:
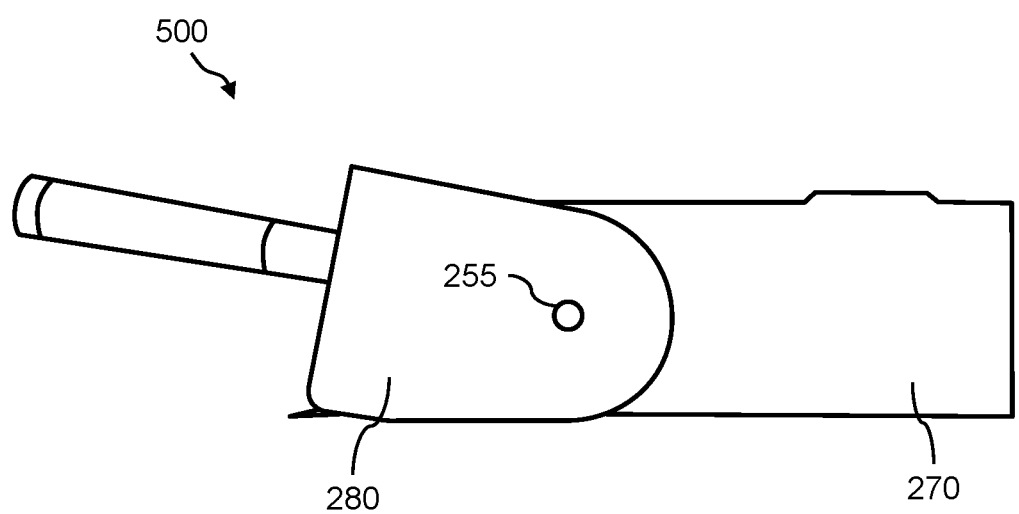
FIG. 12b is a side view of the dustpan in a closed configuration.
Figure 13:
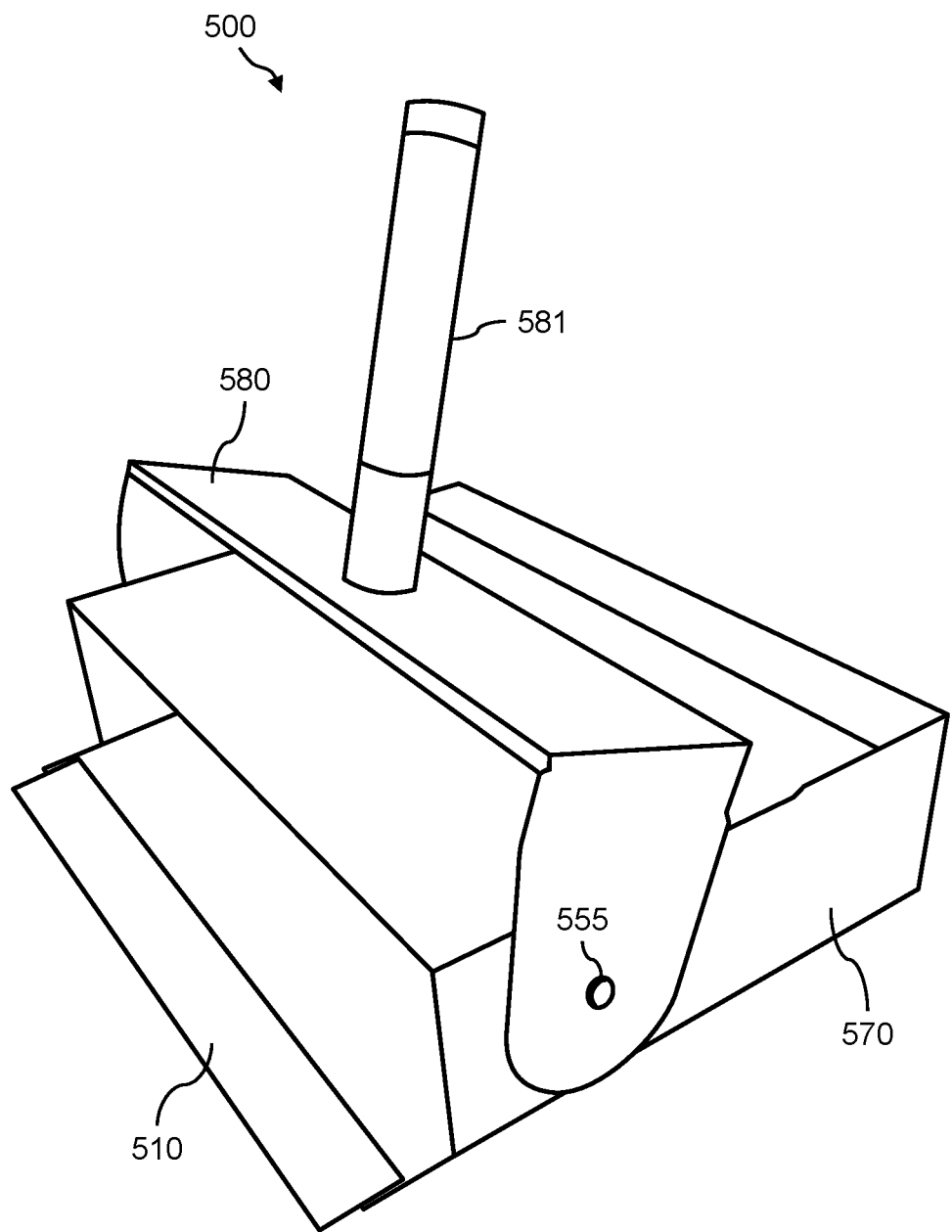
FIG. 13 is a perspective view of the dustpan interacting with a surface.

The side panels 550b of the lid 580 may be coupled to the side panels 550a of the base 570. The side panels 550b may slide over and around the side panels 550a of the base 570, and cover a portion of the side panels 550a of the base 570 (as can be seen in FIGS. 6, 12a, and 12b). The base 570 and the lid 580 may be coupled to one another at the side panels 550a, 550b. Each side panel 550a, 550b may have a hinge point 555. In other embodiments, each side panel 550a of the base may have an aperture configured to align with an aperture of each side panel 550b of the lid 580. When aligned, the apertures may be configured to receive a pin, screw, dowel, or other appropriate fastening mechanism in the art now known or later discovered. The fastening mechanism may be inserted in the apertures to form the hinge point 555.

Alternately, the base 570 may be hingedly connected to the lid 580 at the side panels 550a, 550b. In some embodiments, the hinge point 555 is proximate a center point of the side panels 550b of the lid.

The hinge point 555 may be aligned along the hinge axis 546. Therefore, the hinge point 555 of left side panels 550a, 550b may be located in the same place as the hinge point 555 of the right side panels 550a, 550b. Put another way, the left side panels 550a, 550b may be mirror images of the right side panels 550a, 550b. In some embodiments, the dustpan 500 is symmetrical about a y-z axis extending from a midpoint of a front end of the dustpan 500 to a midpoint of a rear end of the dustpan 500. Alternately, the dustpan 500 is symmetrical along a y-z axis from a center point of the front panel 530 to a center point of the back panel 520.

The lid 580 may further comprise a secure coupling 581 for use with the handle 65 in order to securely couple the handle 65 to the dustpan 500. The secure coupling 581 may include a threaded fastener, hook and loop fasteners, detents, or any other appropriate coupling mechanism in the art now known or later discovered. In embodiments where the secure coupling 581 is a threaded fastener, an attachment end 66 of the handle 65 may also be threaded and configured to be received in the secure coupling 581. The secure coupling 581 may be composed of a biodegradable material. Alternately, the secure coupling may be composed of a sturdier material, such as metal, plastic, polyvinyl chloride, a synthetic plastic polymer, or any other appropriate material in the art now known or later developed.

In some embodiments, the secure coupling 581 is coupled to the lid 580 such that the lid 580 may be maintained in an open position when the coupling 581 is engaged with the handle 65. The secure coupling 581 may be coupled to the lid 580 at the front panel 530b.

The lid 580 may be configured to rotate about the hinge point 555. In some embodiments, both the lid 580 and the base 570 rotate about the hinge axis 546. In an open configuration wherein the base 570 has been temporarily adhered to the floor, lid 580 may rotate approximately 90 degrees such that the front panel 530b of the lid 580 may rest generally parallel the top panel 540a of the base 570. In other embodiments, the lid 580 may rotate about the hinge axis 546 between 45 and 135 degrees. In alternate embodiments, the lid 580 may rotate about the hinge point 555 such that the biological waste may be swept or shoveled into an interior of the dustpan 500.

The front panel 530b may be parallel with the back panel 520a. In other embodiments, the front panel 530b may extend from the base panel 560 at an angle. In some embodiments a top edge of the front panel 530b is closer to the back panel 520a than a bottom edge of the front panel 530b.

In some embodiments, the handle 65 may be connected to the secure coupling 581 at the front panel 530b of the lid 580. The secure coupling 581 may be located at approximately a center point of an outer surface 531b of the front panel 530b. The lid 580 may then rotate approximately 90 degrees about the hinge axis 546 and flip open such that the bottom front panel 530b is substantially in an x-z plane. The handle 65 may then be used to prevent the lid 580 from alternating back to a closed position. In some embodiments, the weight of the handle 65 may assist in maintaining an open position of the dustpan 500. In other embodiments, a user may gently hold the handle 65 to maintain the open position of the dustpan 500. In other embodiments, the handle 65 and coupling 581 may be designed such that the weight of the handle is disposed laterally behind the coupling 581, thus assisting in maintaining an open position of the dustpan 500. In yet other embodiments, the lid 580 may rotate further than 90 degrees around the hinge axis 546 such that a first edge of the lid 580 is in contact with the top panel 540a of the base 570.

After the spill has been absorbed and the waste has been transferred to the dustpan 500, it may be beneficial for a user to transition the dustpan 500 from an open position to a closed position. In order to activate the self-sealing closed position, a user may simply grip the handle 65 and pull upwardly such that the base 580 is suspended in the air. The lid 580 will remain or return to being substantially in the x-z plane, and the base 570 may rotate approximately 90 degrees about the hinge axis 546 and/or hinge point 555. The back panel 520a will now extend along the x-z plane, and the top panel 540a and bottom panel 560a will extend along the x-y plane, and the side panels 550a, 550b will still extend along the y-z plane.

Figure 11:
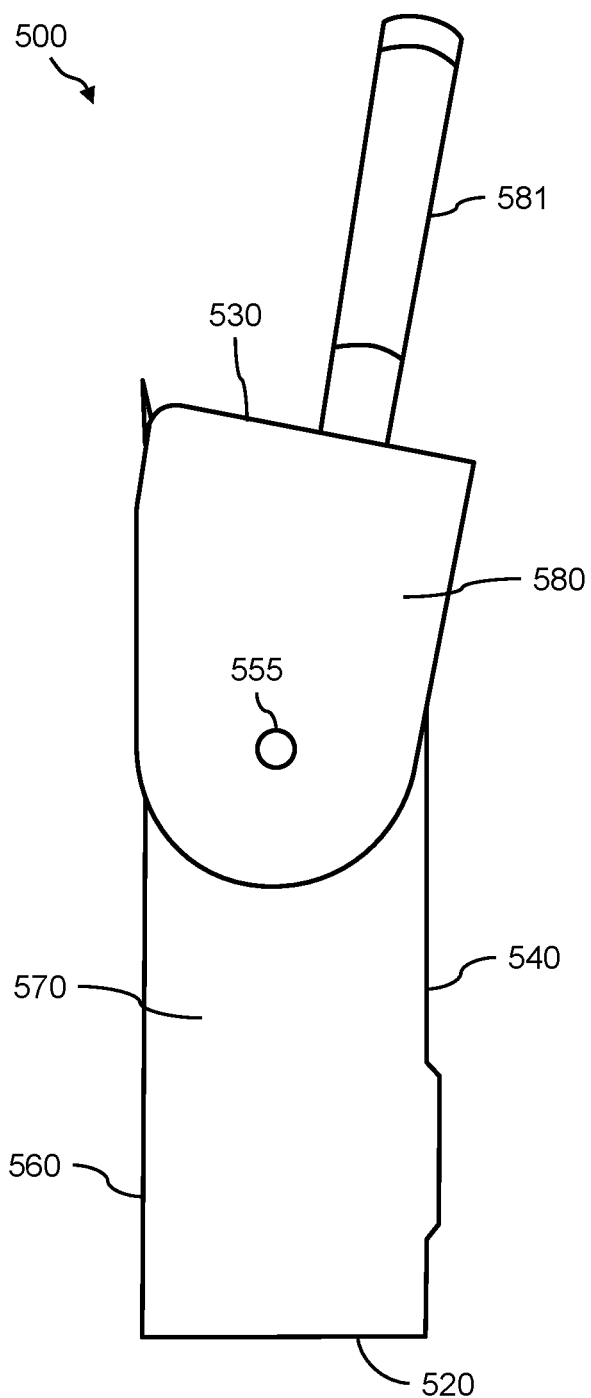
FIG. 11 is a side view of the dustpan as it would be carried in a closed configuration.

The weight of the waste will transfer to the back panel 520a, which is now at or proximate a lowest point of the dustpan, as is shown in FIG. 11. Gravitational forces will maintain the back panel 520a at a low point extending across the x-z plane, which may allow and further encourage the self-sealing mechanism. Because the weight of the waste will be transferred to the back panel 520a, the lid 580 and the base 570 may remain in a closed, self-sealed position.

The self-sealed closed position may be safer for a user because the user can maintain a distance from the waste contained in the dustpan 500. A user is not required to come into close contact with the dustpan 500 in order to lock the lid 580, or transport the dustpan 500. Further, maintaining the lid 580 in a sealed position may prevent the release of biohazardous material or pathogens into the air. Maintaining the closed position may also prevent inadvertent spills as the user transfers the dustpan 500 to the trash.

The self-sealed closed position may be achieved without the use of additional fasteners to couple the lid to the base. In the self-sealed position, the base 570 and the lid 580 may form a closed receptacle having an interior space substantially enclosed by the front panel 530b, rear panel 520a, top panel 540a, bottom panel 560a, and side panels 550a. The top edge 531b of the front panel 530b may be proximate the top panel 540a, and the bottom edge 532b of the front panel 530b may be proximate the bottom panel 560a.

Figure 14:
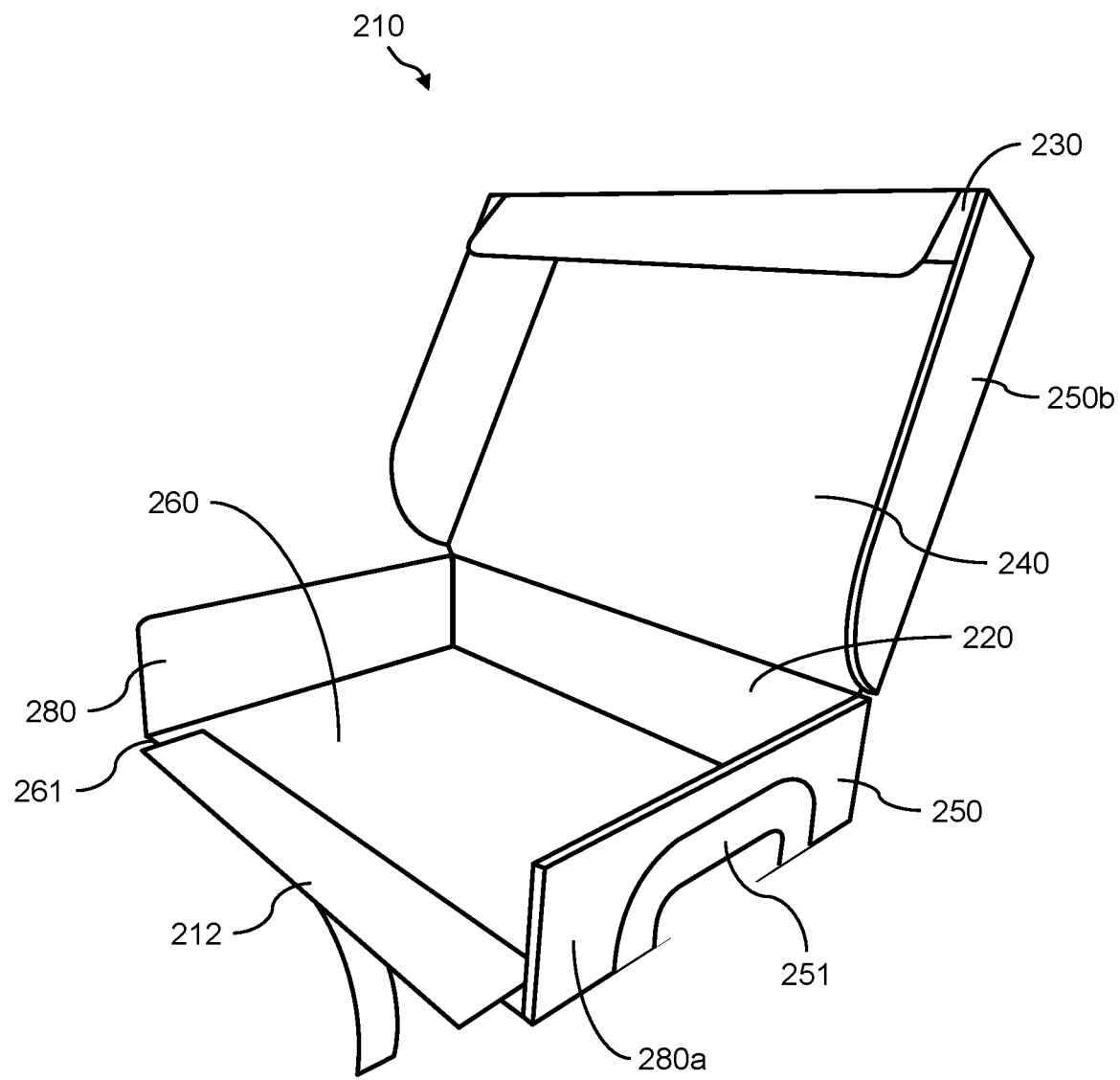
FIG. 14 is a perspective view of an alternate embodiment of a kit showing a case.
Figure 15:
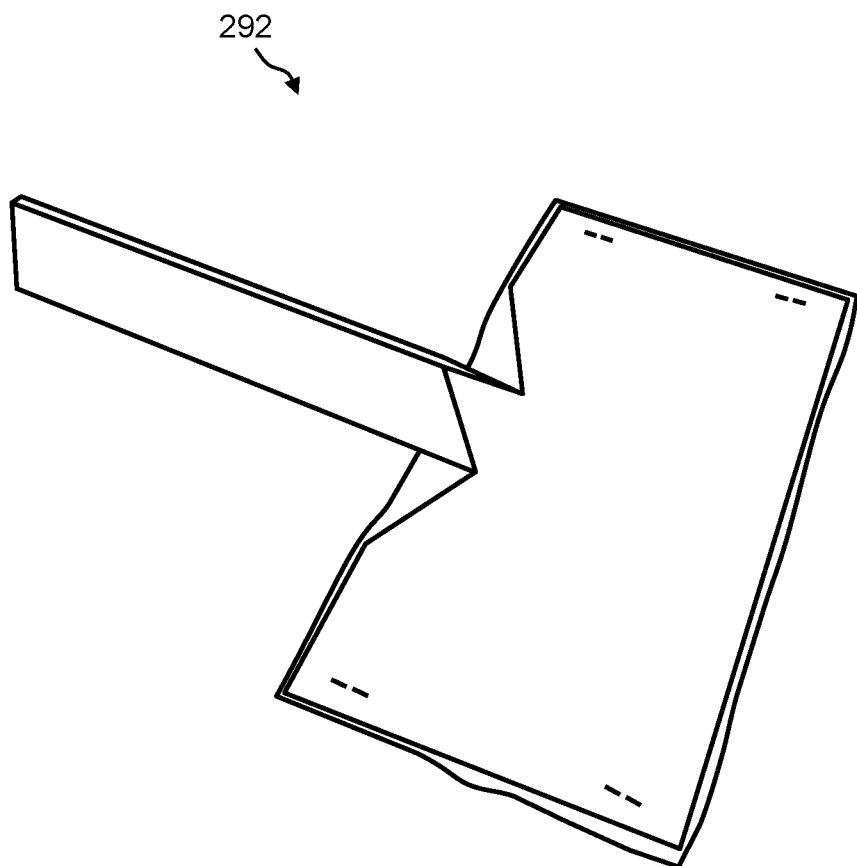
FIG. 15 is a perspective view of a mop.
Figure 16:
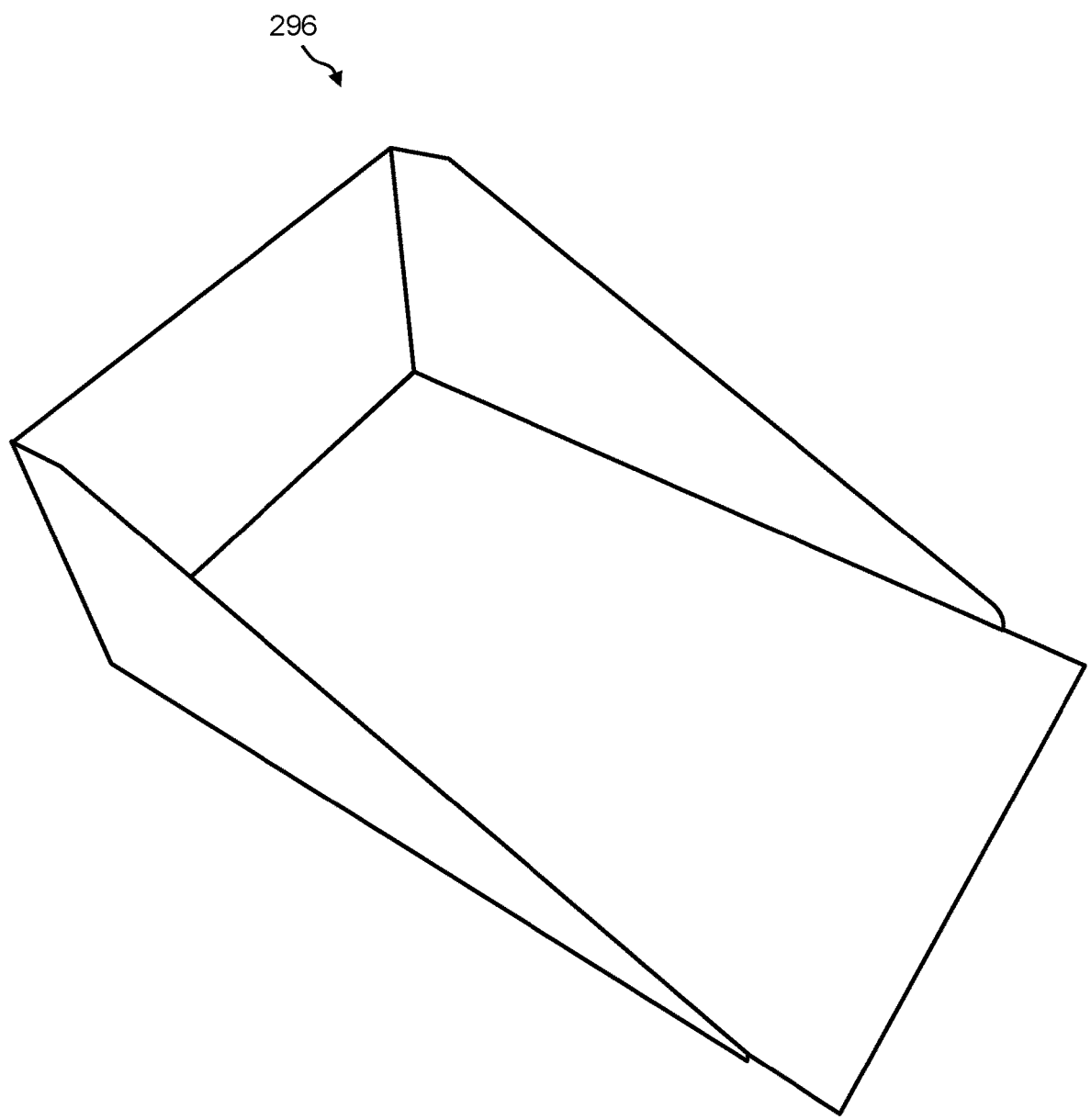
FIG. 16 is a perspective view of a clamshell dustpan.
Figure 17:
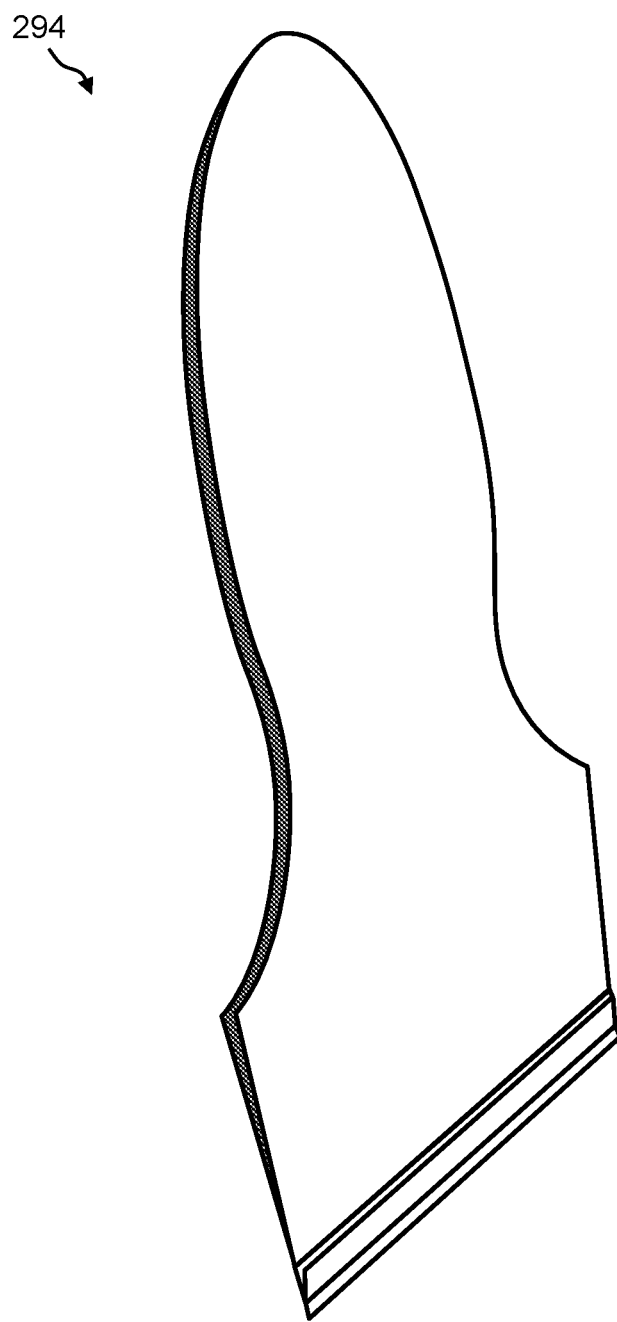
FIG. 17 is a perspective view of a scraper.

In another embodiment, an "Eco Kit" 200 is provided, as is shown in FIG. 14. The exterior kit packaging may be converted from a case 210 holding the kit contents to a dustpan. The case 210 may be a substantially rectangular prism having a front panel 230, a rear panel 220, a top panel 240, a bottom panel 260, and two side panels 250. The case may have a lid portion 280 and a base portion 270, and a hinge axis at the corner proximate a rear edge of the top panel 240 and a top edge of the rear panel 220. Side panels of the base portion 250a may have handles 251. In some embodiments, the handles 251 may be built-in. In some embodiments, the lid portion 280 may be closed hands-free with a user's foot. The kit 200 may include tools 290 such as, among others, a mop 292 (FIG. 15), scraper 294 (FIG. 17), and clamshell dustpan 296 (FIG. 16).

The tools may be configured to fit inside the case 210 in a packaged embodiment. After use of the kit 200 to clean up a spill, it is envisioned that the tools 290 may be placed within the case 210, and the case may be sealed and disposed of (not shown). In some embodiments, the case 210 and tools 290 may be made entirely from biodegradable materials. The case 210 and tools 290 may be made of corrugated cardboard. In other embodiments, the case 210 may have an adhesive strip 212 proximate a lip 261. The adhesive strip 212 may be similar to the adhesive strips described elsewhere in this application. In other embodiments, the lid 280 may have a flap 282 that extends downwardly from the front panel 230 and may be used to seal the case 210 after the waste contents and tools 290 have been deposited in the case 210.

Cleanup Kit Example 2

The present approach is a spill cleanup kit in a variety of embodiments or examples. In some embodiments, the kit may be presented as a vomit cleanup kit in alternative packaging. Such an embodiment may be almost entirely biodegradable, and comprised entirely of non-toxic materials. A user may don personal protective equipment in progress of using the kit. As before, note that the compact nature of the packaged kit makes it portable so that it may be carried about or relocated within a facility. In this case, clearly labeled packaging communicates to all users the application or use for the contents. The cleanup kit items may be deployed about 10 feet from a simulated spill. Optional foldable and disposable caution signs may be erected to close off or secure the area.

The internal packaging for personal protective equipment may be provided in a pouch labeled "Personal Protective Equipment USE FIRST" and contain personal protective equipment for the user. Cleanup kit may include easy to understand instructions, such that even a user without training or experience may understand a safe and effective approach to cleanup of a spill. Personal protective equipment may include equipment tailored for the contemplated use (e.g., an apron, face mask, gown, hair cover, booties/shoe covers, respirator mask, etc.) Optionally, the gown may provide anchors or other assistive technology, such as a neck or head loop (i.e., to secure the top of the gown) or thumb loops (i.e., to secure sleeves underneath gloves), which assist in providing a secure fit. Gloves may typically be donned last. Personal protective equipment may, as applicable, be fabricated from vinyl, laminated papers, latex, nitrile, etc., as desired for the application.

A foldable waste can or trash bin may have a cardboard embodiment. Other materials, such as light, plastic boards may be used; preferably, the material will be lightweight, easily assembled, inexpensive, disposable and easily biodegradable. The trash bin may be unfolded or assembled into its useable configuration. Bin may be provided pre-lined with a trash or waste bag already inserted, simplifying set up by the user. Depending on the application, cleanup kit may also include a desired number of backup waste bags.

This embodiment of cleanup kit may include an absorbent powder, that may be provided in a bag. The bag containing the absorbent powder may be taken from the kit, opened, and its contents sprinkled to cover the spill with such absorbent powder, as needed. In this case, the powder comprises a blend of superabsorbent polymers, expanded perlite, and deodorizing powder. The superabsorbent polymer may be distinct from the super-absorbent polymer described above used in connection with the adhesive strip. Alternately, the same super-absorbent polymer may also be used. The super-absorbent polymer used in connection with the adhesive strip is not in powder form, as the adhesive strip is provided having already been treated with the super-absorbent polymer.

The powder may, for example, include acrylic acid polymer, sodium salt, perlite, and deodorant. In some embodiments, the powder may contain approximately one percent deodorizing powder, approximately 70 percent perlite, and approximately 29 percent superabsorbent polymers. Absorbent powder may be spread up to 10-feet from the center of the spill.

Perlite has been found to be an advantageous additive to the powder mix, as the superabsorbent polymers by itself can form a slick or gel like texture that may be difficult to fully scoop up, and possibly hazardous. Perlite does not gel or slicken when it comes into contact with an aqueous solution, but rather retains its texture. The addition of perlite therefore may result in a powder that is easier to scoop up. Further, the combination powder may be more effective, as it could leave behind less residue. Additionally, the powder with perlite has been found to be safer for users, as users (or others) may not encounter a slick surface upon clean up and disposal of the waste product.

The user in personal protective equipment may also deploy foldable caution signs sufficiently outside the area of the powder covered spill. The user may then distribute or spread disinfectant or surface sanitizer over the powder covered spill; generally, the kit may include sufficient sanitizer so that the user may preserve some for a final or late application.

Next, a user may assemble a dustpan for use. Additional features or design elements for dustpan will be detailed in Kit 3 below; however, note that this embodiment may include a self-closing, foldable cardboard pan, and all components, including the pole extensions, may be largely paper-based and biodegradable. The dustpan in this embodiment may be identical to the dustpan 500 discussed in depth in the first kit example, and is hereby incorporated in its entirety by reference. In general, component tools of kit are preferably paper-based, disposable, and biodegradable. The pole extensions and tools may be configured in a standard size and mating design, such that the extensions may be used with any of the tools, if desired. In some embodiments, tools may be color coded for easy association of parts with matching colors. Pole extensions enable the worker to maintain a safe 3-foot distance from the spill during the cleaning process.

Alternate embodiments of cleanup kit may include a floor scraper, which also may be configured to attach to segments of pole extensions. A floor scraper may be used to slide or drive solid spill matter into a pile, and then into dustpan. With solid matter within the dustpan, the worker may then lift the self-closing dustpan from the floor, thereby detaching any optional sealing tape. After all solid matter has been pushed into dustpan, the user may dispose of the matter in bin. The user may then remove pole extensions from scraper and dustpan, and dispose of scraper and dustpan in waste bin.

With all solid matter removed from a spill, the user may apply sanitizer to thoroughly saturate entire spill site and wait a desired period, such as 30 seconds for sanitation.

The user may then locate the swab or single-use disposable mop and, if applicable, attach its segments of pole extensions. The mop may be used to wipe the surface of spill site. If desired, the user may use all remaining sanitizer, optionally with sanitizer spray, to disinfectant to saturate the spill site and allow it to air dry. Any empty container for sanitizer may similarly be disposed within trash bin. With tools disposed and affected area clear, a user may also remove all protective personal equipment and dispose. If desired, a user may double or triple-bag all waste.

Optionally, cleanup kit may also include swabs or sanitary cloths or "singles" having alcohol for user cleaning. A user, for example, may thoroughly wash hands for a desired period (e.g., 15-20 seconds) and then use cloths to disinfect hands. When spill site is completely dry, users may discard warning signs and reopen the affected area for personnel access.

Cleanup Kit Example 3

Yet another portable embodiment may be presented as a "Body Fluid Spill Kit" which incidentally includes two sets of components, though embodiments may be directed to a single set. Kit may be U.S. Food Code 2-501.11 and OSHA Bloodborne Pathogen Standard 1910.1030 compliant, and may be effective for spills of vomit, blood, or feces. Various forms of packaging and presentations may be used, but it may be convenient for the kit packaging to have a hand grip for transportation to a site of use. The packaged kit may also have a compact nature, which is enabled by the design and material of the included components. A clear package enables a quick review of the contents, such that a user may supplement the contents if desired. In some embodiments the contents or set of components comprise a waste bag, absorbent powder, foodservice grade surface sanitizer, absorbent towels, a floor scraper with a dustpan, gloves, face mask and eye shield, shoe covers, hairnet, and gown or coveralls. Of course, other components may be included, and variations of these components may be suitable for the application; for example, such a kit may be appropriate for use of pole extensions.

A user may bring the kit to the site of a spill. The user may then unpack the components of the kit and select personal protective equipment from the components for donning. Note that in some embodiments simple instructions may be offered to the user. In some embodiments the instructions may be offered separately and on components such as the scraper.

A user may don the personal protective equipment, with gloves, face mask and eye shield, and gown or coveralls. The user may apply surface sanitizer and absorbent powder in the process of stabilizing the site of a spill. In some case, absorbent powder may comprise sodium polyacrylate as a white, granular, odorless polymer that yields a gel-like solid material with the addition of liquids. The user may typically employ one third to one half of the sized container of sanitizer to saturate the spill. In some embodiments, sanitizer may, for example, be an EPA-registered disinfectant effective against HIV, MRSA, *E. coli* and other pathogens, such as a water based mixture of ethyl alcohol (e.g., at about 30%) and isopropyl alcohol, with possibly up to about 1% potassium hydroxide. Such a material may be effective to kill many forms of bacteria in about 30-seconds according to EPA compliance in vitro testing.

In some embodiments, the user may then set up the dustpan for use proximate to the site of the spill. In some embodiments, the dustpan may include integrated sealing tape and an integrated bag. In setting up the dustpan for use, the user may expand the integrated bag. User may then apply the integrated sealing tape to the surface. The dustpan in this embodiment may be identical to the dustpan 500 discussed in depth in the first kit example, and is hereby incorporated in its entirety by reference.

The user may employ scraper to convey spill material into dustpan. Once the spill material has been conveyed into dustpan, the user may then re-apply surface sanitizer to the spill area. The user may wait a predetermined time, such as 30-seconds, to permit the sanitizer to work. The scraper may have been placed within dustpan, which is configured or otherwise sized to receive such tools. The user may employ the mop to clean the spill area, and the mop may also placed into dustpan upon completion of cleaning the spill area. For this embodiment of kit, pole extensions were not desired; however, embodiments may be so modified, depending on the application and desired use.

The user may unseal the adhesive strip and remove the filled dustpan from its position on the floor or deck. The dustpan may then be closed and discarded. The user may then apply surface sanitizer to the area of the spill. Next, the user may wipe the area with an optional towel. Alternatively, the site may simply be permitted to air dry. As with the other embodiments, the user may then discard the personal protective equipment into the trash bag.

The present approach may be embodied in other specific forms without departing from the spirit or essential characteristics thereof. The disclosed embodiments are therefore to be considered in all respects as illustrative and not restrictive, the scope of the present approach being indicated by the claims of the application rather than by the foregoing description, and all changes which come within the meaning and range of equivalency of the claims are therefore intended to be embraced therein. One of ordinary skill in the art should appreciate that numerous possibilities are available, and that the scope of the present approach is not limited by the embodiments described herein.

What is claimed is:

1. A kit for cleaning biological fluids from a surface, the kit comprising:
   at least one protective article of clothing;
   absorbent powder;
   a trash bag;
   surface sanitizer;
   an absorbent towel configured to be used to wipe up the surface after the absorbent powder had absorbed the bodily fluids and had been disposed of;
   a scraper;
   a handle; and
   a dustpan configured to be securely coupled to the handle, the dustpan having a lid and a base, the dustpan further configured to be alternate between an open position and a self-sealing closed position;
   wherein in the closed position the base and lid define an interior volume having a height along a y-axis, a width along an x-axis, and a thickness along a z-axis;
   wherein the absorbent powder is a mixture of a super absorbent polymer and perlite; and
   wherein an adhesive strip is treated with a super-absorbent polymer along proximate edges of the adhesive strip wherein the super-absorbent polymer is configured to react with moisture and form a barrier to seal the edges of the strip to a surface coupled to a lip of the dustpan, the adhesive strip configured to interact with a surface and temporarily engage the dustpan with the surface.

2. The kit of claim 1, wherein the handle is securely and rotatably coupled to the dustpan using a coupling component at a front panel of the lid such that when the dustpan is lifted using the handle, the base naturally rotates about a hinge point from the open position to the closed position due to gravity to retain discarded waste and the lid and the base transition in the closed position.

3. The kit of claim 2, wherein there are two hinge points proximate side panels of the base and lid, wherein the hinge points connect the base and lid.

4. The kit of claim 2, wherein the base rotates approximately 90 degrees when transitioning from the open position resting on a surface to the closed position when the base is lifted entirely off the ground.

5. The kit of claim 1, wherein the absorbent powder further comprises deodorizing powder.

6. The kit of claim 5, wherein the absorbent powder is approximately one percent deodorizing powder, 70 percent perlite, and 29 percent superabsorbent polymers.

7. The kit of claim 1, wherein the adhesive strip is single-sided with a peel-off split-back liner wherein a first end of the adhesive strip has been pre-applied to the dustpan.

8. The kit of claim 1, wherein the base is a unitary construction and the lid is a unitary construction.

9. The kit of claim 1, wherein the lid and the base are configured to rotate about the x-axis.

* * * * *